United States Patent [19]
Fink-Jensen

[11] Patent Number: 5,914,333
[45] Date of Patent: Jun. 22, 1999

[54] TREATMENT OF PSYCHOTIC DISORDERS

[75] Inventor: Anders Fink-Jensen, Kbhv., Denmark

[73] Assignee: Novo Nordisk A/S, Bagsvaerd, Denmark

[21] Appl. No.: 08/899,667

[22] Filed: Jul. 24, 1997

[30] Foreign Application Priority Data

Jul. 31, 1996 [DK] Denmark .................... 0824/96

[51] Int. Cl.⁶ .................................... A61K 31/445
[52] U.S. Cl. ............................ 514/326; 546/212
[58] Field of Search ............................. 514/326

[56] References Cited

U.S. PATENT DOCUMENTS

| | | | |
|---|---|---|---|
| 4,383,999 | 5/1983 | Bondinell et al. | 424/266 |
| 5,354,760 | 10/1994 | Petersen et al. | 514/326 |
| 5,660,861 | 8/1997 | Jao et al. | 424/465 |

FOREIGN PATENT DOCUMENTS

| | | | |
|---|---|---|---|
| 1 952 5598 A1 | 1/1997 | Germany . | |
| 9531976 A1 | 11/1995 | WIPO . | |
| 9615782 A1 | 5/1996 | WIPO . | |
| 96 34606 A1 | 11/1996 | WIPO . | |
| 97 47619 A1 | 12/1997 | WIPO . | |
| 9805330 A1 | 2/1998 | WIPO . | |

OTHER PUBLICATIONS

Mosconi et al Int. J. Clin. Pharmacol. Res. 13/6:331–334 New Anxiolytics in Development, 1993.
Dodrill et al (II) Epilepsia 39(1): 33–42 Effects of Tiagabine Monotherapy on Abilities Adjustment and Need, 1998.
Mohler Schweizerische Rundschau fur Medizin/Praxis:87/6:186–190, 1998.
Beneficial Results of Tiagabine Therapy in Patients with Psychiatric History Kraus et al Epilepsia 38 Suppl 8 106, Dec. 7–10, 1997.
Dodrill et al I Neurology 46 (2 Suppl) A277 Changes in Mental Abilities and Adjustment with Conversion to Tiagabine Monotherapy, Mar. 23–30, 1996.
Nielson et al Eur. J. Pharmacol. 196/3:257–266 Characterization of Tiagabine (No. 328) A New Potent and Selective GABA Uptake Inhibitor in Diazepam or Amphetamine Rats, 1991.

*Primary Examiner*—Shep K. Rose
*Attorney, Agent, or Firm*—Steve T. Zelson, Esq.; Reza Green, Esq.

[57] ABSTRACT

The present invention relates to a method for the treatment of psychotic disorders.

8 Claims, No Drawings

TREATMENT OF PSYCHOTIC DISORDERS

CROSS-REFERENCE TO RELATED APPLICATIONS

This application claims priority under 35 U.S.C. 119 of Danish application 0824/96 filed Jul. 31, 1996, the contents of which are fully incorporated herein by reference.

FIELD OF THE INVENTION

The present invention relates to a method for the treatment of psychotic disorders, in particular psychotic affective disorders and more particular manic disorders.

The present invention also relates to a compound for use in such methods.

The present invention further provides the use of such compound or a pharmaceutically acceptable salt thereof in the manufacture of a medicament for use in the treatment of psychotic disorders, in particular psychotic affective disorders and more particular manic disorders.

BACKGROUND OF THE INVENTION

Bipolar disorder i.e. manic-depressive illness is a cronic disease that affects about 1% of the population. The manic episodes contains symptoms of hyperactivity, insomnia, disorganized behavior, grandiosity and delusions often resulting in severe social impairment.

Lithium or a combination of neuroleptics and benzodiazepines are the most commonly used drugs for the treatment of acute mania (R. H. Gerner: Treatment of acute Mania. Psychiatr Clin North Am (1993) 16:443–460; P. Vestergaard: Treatment and prevention of mania: a Scandinavian perspective. Neuropsychopharm (1992) 7:249–259.).

However, the treatment is often not effective or endowed with various side effects.

Anticonvulsant drugs such as carbamazapine, valproic acid and lamotrigine have more recently proven efficacious as antimanic agents but their mechanism of action is still unclear.( J. Walden and B. Hesslinger: Bedeutung alter und neuer Antiepileptika in der Behandlung psychischer Erkrankungen. Fortschr Neurol Psychiat 63 (1995) 320–335.

P. E. Keck jr., S. L. McElroy and C. B. Nemeroff: Anticonvulsants in the treatment of bipolar disorder. J. Neuropsychiatry Clin Neuroscience (1992) 4:395–405 ).

Danish Patent no. 156398 discloses a class of compounds that exhibit γ-amino butyric acid uptake (GABA-uptake) inhibitory properties and said compounds are valuable in the treatment of epilepsy and other related diseases.

The R-isomer of N-(4,4-di(3-methylthien-2-yl)but-3-enyl)-nipecotic acid, in the following referred to by its generic name, tiagabine (INN) and its pharmaceutically active salts has in particular been found useful in the treatment of epilepsy.

DESCRIPTION OF THE INVENTION

It has now been found that tiagabine also has potential therapeutic utility for treating psychotic disorders, in particular psychotic affective disorders and more particular manic disorders.

Accordingly, the present invention provides a method for treating psychotic disorders, in particular psychotic affective disorders and more particular manic disorders which method comprises administering an effective, non-toxic amount of tiagabine or a pharmaceutically acceptable salt thereof, to human og non-human animals suffering from psychotic disorders, in particular psychotic affective disorders and more particular manic disorders.

The present invention also provides the use of tiagabine or a pharmaceutically acceptable salt thereof in the manufacture of a medicament for use in the treatment of psychotic disorders, in particular psychotic affective disorders and more particular manic disorders.

Examples of pharmaceutically acceptable salts of tiagabine are tiagabine hydrochloride, but tiagabine may also be prepared in the form of other pharmaceutically acceptable salts, especially acid-addition salts, including salts of organic acids and mineral acids.

Examples of such salts include salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid and the like.

Suitable inorganic acid-addition salts include salts of hydrobromic, sulphuric and phosphoric acids and the like.

The acid addition salts may be obtained as the direct products of compound synthesis.

In the alternative, the free base may be dissolved in a suitable solvent containing the appropriate acid, and the salt isolated by evaporating the solvent or otherwise separating the salt and solvent.

A preferred salt is crystalline tiagabine hydrochloride monohydrate.

A tiagabine medicament, for use in the treatment of psychotic disorders, in particular psychotic affective disorders and more particular manic disorders may be prepared by admixture of tiagabine or a salt thereof with an appropriate carrier, which may contain a diluent, binder, filler, disintegrant, flavouring agent, colouring agent, lubricant or preservative in conventional manner.

Pharmaceutical compositions

The compound of the invention, together with a conventional adjuvant, carrier or diluent, and if desired in the form of a pharmaceutically acceptable acid addition salt thereof, may be placed into the form of pharmaceutical compositions and unit dosages thereof, and in such form may be employed as solids, such as tablets or filled capsules, or liquids, such as solutions, sus-pensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of tiagabine commensurate with the intended daily dosage range to be employed. Tablets containing five (5) milligrams of active ingredient or, more broadly, one (1) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhyroxyethoxylated castor oil, gelatine, lactose amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilised and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 1–100 mg/day, when administered to patients, e.g. humans, as a drug.

Examples of tablets which may be prepared by conventional tabletting techniques are:

| COMPOSITION I | | |
|---|---|---|
| Tiagabine hydrochloride | 5.0 | mg |
| Lactosum | 7.0 | mg Ph. Eur. |
| Avicel TM | 31.4 | mg |
| Amberlite TMIRP 88 | 1.0 | mg |
| Magnesii stearas | 0.25 | mg Ph. Eur. |
| or | | |
| COMPOSITION II | | |
| Tiagabine hydrochloride | 8 | mg |
| Polyethylene Glycol 6000, NF | 16 | mg |
| Lactose, anhydrous, NF | 279 | mg |
| δ-Tocopherol, Ph. Eur | 0.8 | mg |
| Talc, Ph. Eur. | 16 | mg |

Pharmacological Effects

The effects of psychomotor stimulants in rodents have been widely used as an animal model of mania (T. W. Robbins and B. J. Sahakian: Animal models of Mania. In: R. H. Belmaker and H. M. van Praag (eds) Mania: An evolving concept. New York: Spectrum (1981) 143–216; R. M. Post, S. R. B. Weiss and A. Pert: Animal models of Mania. In: P. Willner and J. Scheel-Krüger (eds) The Mesolimbic Dopamine System: From motivation to Action. West Sussex: John Wiley and Sons Ltd. (1991) 443–472.) Inhibition of d-amphetamine induced hyperactivity was measured in male NMRI mice (20+–2 g) or in male Sprague Dawley rats (200+–20 g).

The test compounds were injected subcutaneously or intraperitoneally 10 min. before a subcutaneous injection of saline (lithium-carbonate 40 min. before). Twenty minutes following the injection of saline, the animals were placed in a plexiglass box and locomotor activity was measured for 20 min. The activity was measured as interruptionas of infrared photobeams.

A dose of a given test compound that did not block spontaneous locomotor activity was injected subcutaneously or intraperitoneally 10 min. before a subcutaneous injection of d-amphetamine (lithium-carbonate 40 min. before). Twenty minutes following the injection of d-amphetamine, the animals were placed in a plexiglass box and locomotor activity was measured for 20 min.

Psychomotor alterations are one of the core symptoms of mania, which is directly assessed in this model, where d-amphetamine hyperactivity is measured. In addition, clinically effective antimanic drugs such as lithium, carbamazepine and valproate inhibit d-amphetamine induced hyperactivity in this model. Therefore, the actual model is regarded relevant as an animal model of mania.

RESULTS

The GABA uptake inhibitor tiagabine, 10 mg/kg s.c. inhibits d-amphetamine induced hyperactivity in rats.

The GABA uptake inhibitor 1-(2-(((Diphenylmethylene)amino)oxy)ethyl)-1,2,5,6-tetrahydro-3-pyridinecarboxylic acid, 10 mg/kg s.c. inhibits d-amphetamine induced hyperactivity in mice.

Lithium-carbonate, 100 mg/kg i.p. inhibits d-amphetarnine induced hyperactivity in mice.

Carbamazepine, 300 mg/kg i.p. inhibits d-amphetamine induced hyperactivity in mice.

Valproate, 300 mg/kg i.p. inhibits d-amphetamine induced hyperactivity in mice.

I claim:

1. A method of treating psychotic disorders in a human, said method comprising administering an effective, non-toxic amount of tiagabine or a pharmaceutically acceptable salt thereof, to a human suffering from a psychotic disorder.

2. A method of treating manic disorders in a human, said method comprising administering an effective, non-toxic amount of tiagabine or a pharmaceutically acceptable salt thereof, to a human suffering from a manic disorder.

3. A method according to claim 1 wherein said tiagarbine or a pharmaceutically acceptable salt thereof is adapted for oral administration.

4. A method according to claim 1 wherein said tiagabine or a pharmaceutically acceptable salt thereof is adapted for parenteral administration.

5. A method according to claim 1 wherein the tiagabine or a pharmaceutically acceptable salt thereof is in a unit dose form containing from 0.05 to 100 mg of tiagabine or a pharmaceutically acceptable salt thereof.

6. A method according to claim 2 wherein the tiagabine or a pharmaceutically acceptable salt thereof is in a unit dose form containing from 0.05 to 100 mg of tiagabine or a pharmaceutically acceptable salt thereof.

7. A method according to claim 2 wherein the tiagabine or a pharmaceutically acceptable salt thereof is adapted for oral administration.

8. A method according to claim 2 wherein the tiagabine or a pharmaceutically acceptable salt thereof is adapted for parenteral administration.

* * * * *